Dec. 29, 1959 S. J. HICKS Plant Pat. 1,892
ROSE PLANT
Filed Feb. 9, 1959
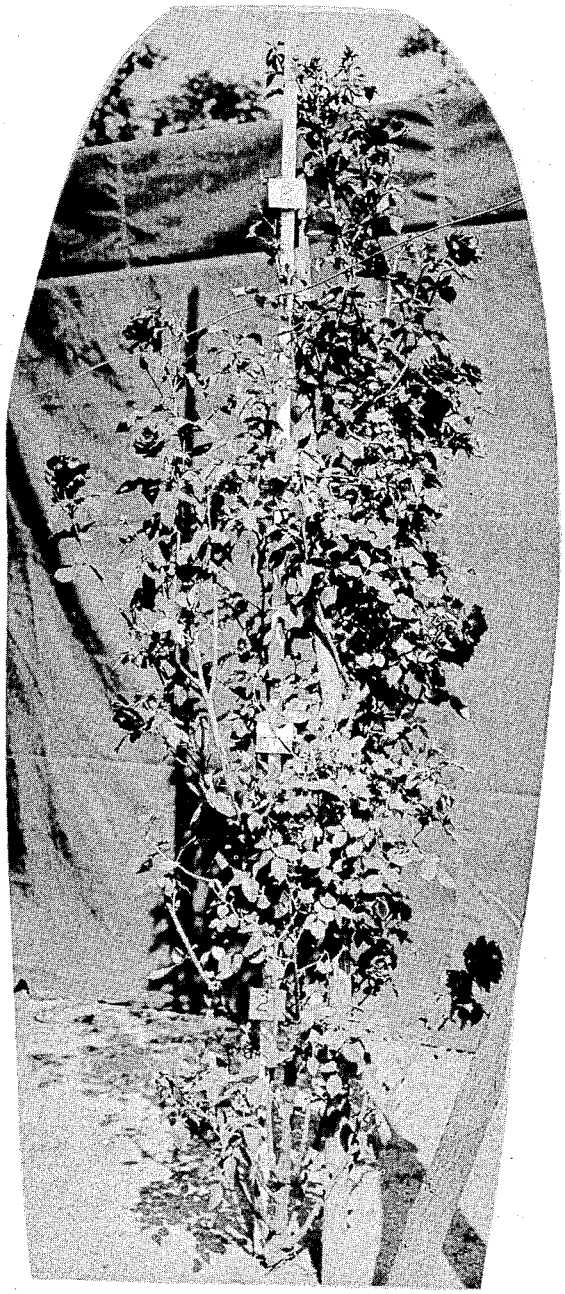
INVENTOR
Sam J. Hicks
BY Robb & Robb
ATTORNEYS United States Patent Office Plant Pat. 1,892
Patented Dec. 29, 1959

1,892

ROSE PLANT

Sam J. Hicks, Tyler, Tex., assignor, by mesne assignments, to The Conard-Pyle Company, West Grove, Pa., a corporation of Pennsylvania Application February 9, 1959, Serial No. 792,236

1 Claim. (Cl. 47—61)

The present invention relates to a new and distinct variety of rose plant of the climbing hybrid tea class, which originated as a sport of the bush hybrid tea variety "President Eisenhower" (Plant Patent No. 1,217).

This new variety was initially discovered by me amongst a block of several hundred plants of the variety "President Eisenhower" which were being grown under my supervision and control on property under my control in Smith County, near Tyler, Texas. During my cultivation of these plants, my attention was attracted to one particular plant which exhibited a climbing habit, as distinguished from the normal bush habit of growth of the variety "President Eisenhower." Upon closer examination of this plant, I found that it had sported, and I thereupon took steps to preserve the sport, keep it under observation, and later to asexually reproduce the same. Continued observations of the original plant and the asexual reproductions thereof, as performed by budding at Tyler, Texas and at West Grove, Pennsylvania, fully confirmed the climbing habit of the new sport and conclusively established that this climbing habit comes true to form and is transmissible through succeeding propagations.

The climbing habit of the new variety aforesaid is evidenced by long shoots attaining a height of from 8 to 12 feet, which gear flowers at the terminals of the shoots. The new variety is further characterized as to novelty by its short axillary branches which bear flowers and foliage corresponding to those of its parent variety "President Eisenhower," with the flowers being Rose Red in general color tonality. It is also characterized by floriferousness and exceptional remontance which are unusual in a variety of the climbing hybrid tea class.

So far as I am aware, the parent variety "President Eisenhower" has never exhibited a climbing habit, and its growth has been that of the average bush hybrid tea rose, while the new sport is differentiated therefrom by its vigorous and upright climbing and branching habit.

The accompanying drawing shows a specimen plant of the new variety which is illustrative of the typical climbing habit of growth, as indicated by the markings on a measuring stake shown in association with the plant and graduated in feet.

In view of the similarities in general characteristics between the new variety and its parent "President Eisenhower," excepting for the aforementioned distinctions, it is unnecessary to describe the new variety in detail since it conforms substantially to the detailed description appearing in Plant Patent No. 1,217, dated September 22, 1953, to which reference may be readily had.

I claim:

A new and distinct variety of rose plant of the climbing hybrid tea class, substantially as herein shown and described, characterized particularly as to novelty by its general similarity to its parent variety "President Eisenhower" (Plant Patent No. 1,217), but being principally distinguished therefrom by its long climbing shoots which bear flowers at the terminals thereof, short axillary branches on which are borne flowers and foliage corresponding to those of the parent variety aforesaid, and exceptional floriferousness and remontance which are unusual in a rose variety of this class.

No references cited.